(12) United States Patent
Miller et al.

(10) Patent No.: US 6,459,009 B1
(45) Date of Patent: Oct. 1, 2002

(54) TWO-STAGE QUENCH TOWER FOR USE WITH OXYGENATE CONVERSION PROCESS

(75) Inventors: Lawrence W. Miller, Palatine; John J. Senetar, Naperville, both of IL (US)

(73) Assignee: UOP LLC, Des Plaines, IL (US)

(*) Notice: Subject to any disclaimer, the term of this patent is extended or adjusted under 35 U.S.C. 154(b) by 0 days.

(21) Appl. No.: 09/990,466

(22) Filed: Nov. 21, 2001

Related U.S. Application Data (62) Division of application No. 09/691,865, filed on Oct. 19, 2000.

(51) Int. Cl.$^7$ .............................. C07C 7/00; C07C 7/10
(52) U.S. Cl. .................. 585/809; 585/910; 585/834; 585/868
(58) Field of Search .................. 585/809, 910, 585/834, 868

(56) References Cited

U.S. PATENT DOCUMENTS

| | | | | |
|---|---|---|---|---|
| 3,674,887 A | * | 7/1972 | Clay | 585/621 |
| 3,928,483 A | | 12/1975 | Chang et al. | 585/322 |
| 4,025,575 A | | 5/1977 | Chang et al. | 585/640 |
| 4,044,061 A | | 8/1977 | Chang et al. | 585/402 |
| 4,252,479 A | | 2/1981 | Scherfenberg | 406/182 |
| 4,447,669 A | | 5/1984 | Hamon et al. | 585/640 |
| 4,496,786 A | | 1/1985 | Santilli et al. | 585/640 |
| 4,499,314 A | | 2/1985 | Seddon et al. | 585/408 |
| 4,547,616 A | | 10/1985 | Avidan et al. | 585/640 |
| 4,677,242 A | | 6/1987 | Kaiser | 585/638 |
| 4,788,042 A | | 11/1988 | Marsh et al. | 422/235 |
| 4,843,183 A | | 6/1989 | Inui | 585/640 |
| 4,851,606 A | | 7/1989 | Ragonese et al. | 585/640 |
| 4,861,938 A | | 8/1989 | Lewis et al. | 585/640 |
| 4,973,792 A | | 11/1990 | Lewis et al. | 585/638 |
| 5,095,163 A | | 3/1992 | Barger | 585/640 |
| 5,126,308 A | | 6/1992 | Barger et al. | 502/214 |
| 5,191,141 A | | 3/1993 | Barger et al. | 585/640 |

FOREIGN PATENT DOCUMENTS

WO    WO 99/55650    11/1999

\* cited by examiner

*Primary Examiner*—Thuan D. Dang
(74) *Attorney, Agent, or Firm*—John G. Tolomei; Frankss Molinaro; Mark Goldberg

(57) ABSTRACT

The invention is a process for recovering heat and removing impurities from a reactor effluent stream withdrawn from a fluidized exothermic reaction zone for conversion of oxygenates into light olefins from an oxygenate feedstream. The process comprises a two-stage quench tower system to remove water from the reactor effluent stream in the first tower and recover heat from the reactor effluent to at least partially vaporize the feedstream by indirect heat exchange between the oxygenate feedstream and either a first stage overhead stream or a first stage pumparound stream. A drag stream withdrawn from the first tower comprises the majority of the impurities and higher boiling oxygenates. The second stage tower further removes water and provides a purified water stream which requires minimal water stripping to produce a high purity water stream. The invention concentrates the impurities into a relatively small stream and results in significant energy and capital savings.

8 Claims, 4 Drawing Sheets

TWO-STAGE QUENCH TOWER FOR USE WITH OXYGENATE CONVERSION PROCESS

CROSS-REFERENCE TO RELATED APPLICATION

This application is a Division of copending application Ser. No. 09/691,865 filed Oct. 19, 2000, the contents of which are hereby incorporated by reference in its entirety.

FIELD OF THE INVENTION

This invention relates to a process for the production of light olefins from an oxygenate feedstream. More specifically the invention relates to a process for the removal of impurities and recovery of heat from the exothermic process for the conversion of oxygenates to olefins.

BACKGROUND OF THE INVENTION

Light olefins have traditionally been produced through the process of steam or catalytic cracking. Because of the limited availability and high cost of petroleum sources, the cost of producing light olefins from such petroleum sources has been steadily increasing. Light olefins serve as feeds for the production of numerous chemicals. As the emerging economies of the Third World strain toward growth and expansion, the demand for light olefins will increase dramatically.

The search for alternative materials for light olefin production has led to the use of oxygenates such as alcohols and, more particularly, to the use of methanol, ethanol, and higher alcohols or their derivatives. These alcohols may be produced by fermentation or from synthesis gas. Synthesis gas can be produced from natural gas, petroleum liquids, and carbonaceous materials including coal, recycled plastics, municipal wastes, or any organic material. Thus, alcohol and alcohol derivatives may provide non-petroleum based routes for the production of olefin and other related hydrocarbons.

Molecular sieves such as microporous crystalline zeolite and non-zeolitic catalysts, particularly silicoaluminophosphates (SAPO), are known to promote the conversion of oxygenates to hydrocarbon mixtures. Numerous patents describe this process for various types of these catalysts: U.S. Pat. Nos. 3,928,483; 4,025,575; 4,252,479; 4,496,786; 4,547,616; 4,677,242; 4,843,183; 4,499,314; 4,447,669; 5,095,163; 5,191,141; 5,126,308; 4,973,792; and 4,861,938.

The process may be generally conducted in the presence of one or more diluents which may be present in the oxygenate feed in an amount between about 1 and about 99 molar percent, based on the total number of moles of all feed and diluent components fed to the reaction zone (or catalyst). U.S. Pat. Nos. 4,861,938 and 4,677,242 particularly emphasize the use of a diluent combined with the feed to the reaction zone to maintain sufficient catalyst selectivity toward the production of light olefin products, particularly ethylene. The above U.S. patents are hereby incorporated by reference.

The conversion of oxygenates to olefins takes place at a relatively high temperature, generally higher than about 250° C., preferably higher than about 300° C. In the conversion of oxygenates to olefins, as significant amount heat is released in the highly exothermic reaction. Because the reactor effluent typically is at a higher temperature than the temperature of feedstock, many methods and schemes have been proposed to manage the heat of reaction generated from the process in order to avoid problems in the operation of the process. Such events as temperature surges and hot spots in the reactor will increase the rate of catalyst deactivation and result in the production of undesirable by products such as paraffins including: methane, ethane, and propane or other undesirable by products such as carbon monoxide or coke. Processes are sought which effectively use the heat of reaction which was transferred to the reactor effluent to avoid operating problems while reducing the overall utility consumption in the conversion of the oxygenate feedstock to produce light olefins and while minimizing the production of waste streams from the process.

In a conventional naphtha cracking process for the production of light olefins, the naphtha charge stock is passed to a cracking furnace to thermally convert larger hydrocarbons into a furnace effluent comprising smaller olefinic hydrocarbons. Typically, the furnace effluent is quenched first by indirect exchange, then by an oil quench, and lastly with a water quench to cool the furnace effluent and to separate the light olefin products from any heavy hydrocarbon or pygas (pyrolysis gasoline) phase which was found in the cracking step. In the present invention, the light olefins are produced by the catalytic conversion of an oxygenate, which also produces about one mole of water for every mole of oxygenate converted. When the oxygenate is converted in the presence of a non-zeolitic molecular sieve such as SAPO-34 or SAPO-17, there is essentially no heavy hydrocarbon phase formed. Furthermore, the present invention is carried out in a fluidized bed reactor which can result in the carryover of catalyst fines from the fluidized bed reactor in the reactor effluent stream. Therefore, quench schemes are sought which recover the heat of reaction from the reactor effluent, while minimizing the production of aqueous waste streams.

These and other disadvantages of the prior art are overcome by the present invention, and a new improved process for conversion of oxygenates to hydrocarbons is provided.

SUMMARY OF THE INVENTION

The present invention provides a process for converting an oxygenate to light olefins with improved heat recovery from reactor effluent streams and improved waste recovery which minimizes overall utility requirements. In the present process, the reactor effluent is quenched with an aqueous stream in a two-stage process to facilitate the separation of hydrocarbon gases from any entrained catalyst fines, remove water and any heavy byproducts such as $C_6^+$ hydrocarbons. In addition, the process of the present invention avoids the previously unknown problem of the build up of corrosive materials, particularly organic acids such as acetic, formic and propanoic acid in the operation of a conventional single column quench system. It was discovered that the reactor effluent can contain small amounts of acetic acid which could build up in conventional quench process schemes. According to the present invention, the reactor effluent is first passed to a first stage quench tower wherein the reactor effluent is contacted with a relatively pure aqueous stream and a neutralizing agent, introduced at the top of the quench tower, to provide a hydrocarbon vapor stream and a first stage bottoms stream or waste water stream. A portion of the waste water stream withdrawn from the bottom of the quench tower is recycled to the quench tower at a point above where the reactor effluent is introduced to the quench tower. In the process of the present invention, the waste water stream produced from the first stage quench tower is a much smaller drag stream than would be produced by a single quench tower and the waste water stream of the present invention comprises heavy organic oxygenates and byproducts, such as high molecular weight alcohols and ketones, and neutralized organic acid components, in addition to any carryover of catalyst fines. Heat integration with the reactor feedstream at the particular points in the process with the hydrocarbon vapor stream withdrawn from the quench tower and with the product water from the bottom of the water stripper provide improved overall heat recovery from the reactor and provide improved operating stability for the overall process.

In one embodiment, the present invention is a process using a two-stage quench for recovering heat and removing impurities from a reactor effluent stream withdrawn from a fluidized exothermic reaction zone. The process comprises the steps of passing a preheated feedstream comprising an oxygenate to an intercondenser to at least partially vaporize the preheated feedstream by indirect heat exchange to provide a partially vaporized feedstream. The partially vaporized feedstream is passed to a feed vaporizer to fully vaporize the partially vaporized feedstream to provide a vaporized feedstream. The vaporized feedstream is passed to a feed side of a feed superheater having a feed side and an effluent side to raise the vaporized feedstream to effective conversion conditions by indirect heat exchange with a reactor effluent stream to provide a superheated feedstream. The superheated feedstream is passed to the fluidized exothermic reaction zone and therein the superheated feedstream is contacted with a particulate catalyst at conversion conditions to at least partially convert the oxygenate to produce the reactor effluent stream comprising light olefins, impurities, water and catalyst particles. The reactor effluent stream is passed to the effluent side of the feed superheater to cool the reactor effluent stream to provide a desuperheated vapor effluent stream. The desuperheated vapor effluent stream is passed to a first stage tower of a two-stage quench zone comprising the first stage tower and a second stage tower. An overhead stream comprising the light olefins and a first stage bottoms stream comprising impurities, catalyst particles, and water are recovered from the first stage tower. A first portion of the first stage bottoms stream and a neutralization stream are returned to an upper portion of the first stage tower. At least a second portion of the first stage bottoms stream is withdrawn from the process as a drag stream. The overhead stream is passed to the intercondenser to cool the overhead stream by indirect heat exchange with the preheated feedstream to provide a cooled overhead stream. The cooled overhead stream is passed to the second stage tower to separate the light olefins and water to provide a vapor product stream comprising light olefins and a purified water stream. A first portion of the purified water stream is returned to the upper portion of the first stage tower, a second portion of the purified water stream is cooled in a product heat exchanger to provide a cooled purified water stream, and the cooled purified water stream is returned to an upper portion of the second stage tower. A third portion of the purified water stream is passed to a water stripper column to provide a water stripper overhead stream and a highly purified water stream. A feedstream is preheated in a feed preheater by indirect heat exchange with the highly purified water stream to produce the preheated feedstream.

In another embodiment, the invention is a process using a two-stage quench for recovering heat and removing impurities from a reactor effluent stream withdrawn from a fluidized exothermic reaction zone. The process comprises the steps of passing a preheated feedstream comprising an oxygenate to an intercooler to at least partially vaporize the preheated feedstream by indirect heat exchange to provide a partially vaporized feedstream. The partially vaporized feedstream is passed to a feed vaporizer to fully vaporize the partially vaporized feedstream to provide a vaporized feedstream. The vaporized feedstream is passed to a feed side of a feed superheater having a feed side and an effluent side to raise the vaporized feedstream to effective conversion conditions by indirect heat exchange with a reactor effluent stream to provide a superheated feedstream. The superheated feedstream is passed to the fluidized exothermic reaction zone and therein the superheated feedstream is contacted with a particulate catalyst at conversion conditions to at least partially convert the oxygenate to produce the reactor effluent stream comprising light olefins, impurities, water and catalyst particles. The reactor effluent stream is passed to the effluent side of the feed superheater to cool the reactor effluent stream to provide a desuperheated vapor effluent stream. The desuperheated vapor effluent stream is passed to a first tower of a two-stage quench zone comprising the first tower and a second tower and an overhead stream comprising the light olefins and a first stage bottoms stream comprising impurities, catalyst particles, and water are recovered. A first portion of the first stage bottoms stream is withdrawn from the process as a drag stream. A second portion of the first stage bottoms stream and a neutralization stream are returned to provide a first stage admixture. The first stage admixture stream is passed to the intercooler to cool the first stage admixture by indirect heat exchange with the feedstream to provide a cooled first stage admixture. The first stage admixture is returned to an upper portion of the first tower. The cooled overhead stream is passed to the second tower to separate the light olefins and water to provide a vapor product stream comprising light olefins and a purified water stream. A first portion of the purified water stream is cooled in a product heat exchanger to provide a cooled purified water stream, and the cooled purified water stream is returned to an upper portion of the second tower. A third portion of the purified water stream is passed to a water stripper column to provide a water stripper overhead stream and a highly purified water stream. A feedstream is preheated in a feed preheater by indirect heat exchange with the highly purified water stream to produce the preheated feedstream.

In a further embodiment, the present invention is a two-stage quench tower process for removing impurities from a superheated reactor effluent stream withdrawn from an oxygenate conversion complex. The process comprises the steps of passing the superheated reactor effluent stream comprising light olefin, water, and organic acids to a feed/effluent exchanger to desuperheat the superheated reactor effluent stream by indirect exchange with a vaporized feedstream to provide a desuperheated stream. The desuperheated stream is passed to a first tower of a two-stage quench zone containing a first tower and a second tower. The desuperheated stream is contacted in an upper portion of the first tower with a neutralized water stream to condense at least a portion of the water to provide a first stage bottoms stream comprising water and neutralized organic acids and a first stage overhead stream comprising light olefins and water. The first stage overhead stream is passed to the second tower and is therein contacted with a cooled purified water stream to provide a light olefin product stream and a purified water stream. A first portion of the purified water stream is cooled to provide the cooled purified water stream. A second portion of the purified water stream is passed to a water stripper column to provide a high purity water stream and a stripper overhead stream. The stripper overhead stream is admixed with the first stage overhead stream, and the first stage overhead stream is cooled prior to passing the first stage overhead stream to the second stage tower, or a second portion of the purified water stream is passed to a water stripper to provide a high purity water stream and a stripper overhead stream, a portion of the first stage bottoms stream is cooled and admixed with a neutralization stream and a third portion of the purified water stream to provide the neutralized water stream. A fourth portion of the purified water stream is returned to the first tower.

DETAILED DESCRIPTION OF THE INVENTION

This invention comprises a process for the catalytic conversion of a feedstock comprising one or more aliphatic hetero compounds comprising alcohols, halides, mercaptans, sulfides, amines, ethers, and carbonyl compounds or mixtures thereof to a hydrocarbon product containing light olefinic products, i.e., $C_2$, $C_3$ and/or $C_4$ olefins. The feedstock is contacted with a silicoaluminophosphate molecular sieve at effective process conditions to produce light olefins. Silicoaluminophosphate molecular sieves which produce light olefins are generally employable in the instant process. The preferred silicoaluminophosphates are those described in U.S. Pat. No. 4,440,871. Silicoaluminophosphate molecular sieves employable in the instant process are more fully described hereinafter.

In the instant process the feedstream comprises an oxygenate. As used herein, the term "oxygenate" is employed to include alcohols, ethers, and carbonyl compounds (aldehydes, ketones, carboxylic acids, and the like). The oxygenate feedstock preferably contains from 1 to about 10 carbon atoms and, more preferably, contains from 1 to about 4 carbon atoms. Suitable reactants include lower straight or branched chain alkanols, and their unsaturated counterparts. Representatives of suitable oxygenate compounds include methanol, dimethyl ether, ethanol, diethyl ether, methylethyl ether, formaldehyde, dimethyl ketone, acetic acid, and mixtures thereof.

In accordance with the process of the present invention, an oxygenate feedstock is catalytically converted to hydrocarbons containing aliphatic moieties such as—but not limited to—methane, ethane, ethylene, propane, propylene, butylene, and limited amounts of other higher aliphatics by contacting the aliphatic hetero compound feedstock with a preselected catalyst. A diluent is required to maintain the selectivity of the catalyst to produce light olefins, particularly ethylene and propylene. The use of steam as the diluent provides certain equipment cost and thermal efficiency advantages. The phase change between steam and liquid water can be employed to advantage in transferring heat between the feedstock and the reactor effluent, and the separation of the diluent from the product requires simple condensation of the water to separate the water from the hydrocarbons. Ratios of 1 mole of feed to about 0.1–5 moles of water have been disclosed.

The oxygenate conversion process of the present invention is preferably conducted in the vapor phase such that the oxygenate feedstock is contacted in a vapor phase in a reaction zone with a molecular sieve catalyst at effective conversion conditions to produce olefinic hydrocarbons, i.e., an effective temperature, pressure, WHSV and, optionally, an effective amount of diluent, correlated to produce olefinic hydrocarbons. The process is affected for a period of time sufficient to produce the desired light olefin products. The oxygenate conversion process is effectively carried out over a wide range of pressures, including autogenous pressures. At pressures between about 0.001 atmospheres (0.76 torr) and about 1000 atmospheres (760,000 torr), the formation of light olefin products will be affected although the optimum amount of product will not necessarily form at all pressures. The preferred pressure is between about 0.01 atmospheres (7.6 torr) and about 100 atmospheres (76,000 torr). More preferably, the pressure will range from about 1 to about 10 atmospheres. The pressures referred to herein for the process are exclusive of the inert diluent, if any, that is present and refer to the partial pressure of the feedstock as it relates to oxygenate compounds and/or mixtures thereof. The temperature which may be employed in the oxygenate conversion process may vary over a wide range depending, at least in part, on the selected molecular sieve catalyst. In general, the process can be conducted at an effective temperature between about 200° and about 700° C.

In the oxygenate conversion process of the present invention, it is preferred that the catalysts have relatively small pores. Preferably, the small pore catalysts have a substantially uniform pore structure, e.g., substantially uniformly sized and shaped pore with an effective diameter of less than about 5 Angstroms. Suitable catalyst may comprise non-zeolitic molecular sieves and a matrix material.

Non-zeolitic molecular sieves include molecular sieves which have the proper effective pore size and are embraced by an empirical chemical composition, on an anhydrous basis, expressed by the empirical formula:

where EL is an element selected from the group consisting of silicon, magnesium, zinc, iron, cobalt, nickel, manganese, chromium and mixtures thereof, x is the mole fraction of EL and is at least 0.005, y is the mole fraction of Al and is at least 0.01, z is the mole fraction of P and is at least 0.01 and x+y+z=1. When EL is a mixture of metals, x represents the total amount of the element mixture present. A preferred embodiment of the invention is one in which the element (EL) content varies from about 0.005 to about 0.05 mole fraction in which EL is silicon (usually referred to as SAPO). The SAPOs which can be used in the instant invention are any of those described in U.S. Pat. Nos. 4,440,871; 5,126,308 and 5,191,141 which are hereby incorporated by reference. Especially preferred SAPOs include the SAPO-34 and SAPO-17.

The preferred oxygenate conversion catalyst may be, and preferably is, incorporated into solid particles in which the catalyst is present in an amount effective to promote the desired hydrocarbon conversion. In one aspect, the solid particles comprise a catalytically effective amount of the catalyst and at least one matrix material, preferably selected from the group consisting of binder materials, filler materials, and mixtures thereof to provide a desired property or properties, e.g., desired catalyst dilution, mechanical strength, and the like to the solid particles. Such matrix materials are often, to some extent, porous in nature and may or may not be effective to promote the desired hydrocarbon conversion. Filler and binder materials include, for example, synthetic and naturally occurring substances such as metal oxides, clays, silicas, aluminas, silica-aluminas, silica-magnesias, silica-zirconias, silica-thorias, silica-berylias, silica-titanias, silica-alumina-thorias, silica-alumina-zirconias, alumino-phosphates, mixtures of these and the like. If matrix materials, e.g., binder and/or filler materials, are included in the catalyst composition, the non-zeolitic molecular sieves preferably comprise about 1 to 99 percent, more preferably about 5 to about 90 percent and still more preferably about 10 to about 80 percent, by weight of the total composition. The preparation of solid particles comprising catalyst and matrix materials is conventional and well known in the art and, therefore, need not be discussed in detail herein.

During the oxygenate conversion reaction, a carbonaceous material, i.e., coke, is deposited on the catalyst. The carbonaceous deposit material has the effect of reducing the number of active sites on the catalyst which thereby affects the extent of the conversion. During the conversion process a portion of the coked catalyst is withdrawn from the reaction zone and regenerated to remove at least a portion of the carbonaceous material and returned to the oxygenate conversion reaction zone. Depending upon the particular catalyst and conversion, it can be desirable to substantially remove the carbonaceous material e.g., to less than 1 weight percent, or only partially regenerate the catalyst, e.g., to from about 2 to 30 weight percent carbon. Preferably, the regenerated catalyst will contain about 0 to 20 percent and more preferably from about 0 to 10 percent carbon. Additionally, during regeneration there can be oxidation of sulfur and in some instances nitrogen compounds along with the removal of metal materials from the catalyst. Moreover, regeneration conditions can be varied depending upon catalyst used and the type of contaminant material present upon the catalyst prior to its regeneration. The details concerning the conditions for regeneration are known to those skilled in the art and need not be further disclosed herein.

The oxygenate conversion process of the instant invention will be further illustrated in terms of a methanol-to-olefin (MTO) process which produces light olefins including ethylene and propylene from methanol. The reaction products which are withdrawn from the MTO reactor must be cooled and separated from water, a byproduct of the conversion, in a quench tower before the olefin products are recovered. In the quench tower, most of the water is condensed and the light hydrocarbons and light oxygenates are removed from the top of the quench tower as an overhead stream and the water is removed from the bottom of the quench tower. Water removed from the quench tower comprises some dissolved light hydrocarbons and heavy byproducts including heavy oxygenates including alcohols and ketones which have a normal boiling point greater than or equal to water and which must be removed by stripping the water heavy byproducts with light gases such as steam or nitrogen. The feedstream passed to an MTO reactor can be refined methanol (essentially pure), or raw methanol containing water comprising up to about 30 weight percent water. The feedstream is heated and vaporized prior to being charged to the fluidized bed MTO reactor. This requires a considerable amount of energy. Therefore, it is necessary to recover as much as energy of the reactor effluent and use it to heat and vaporize the feedstream. However, water is substantially the only condensation product in the quench tower. Thus, the operating temperatures within the quench tower closely approach the bubble/dew point of pure water at the operating pressure. Although methanol and water have a boiling point differential of over 16° C. (60° F.), there is a difference in operating pressure between the methanol vaporization and the water condensation stages. This differential is due to the pressure drop through heat exchangers, the MTO reactor, piping, etc. This pressure differential results in closing the difference between the feed vaporization and product condensation temperatures, making meaningful heat exchange difficult. The presence of any water in the methanol feed, depresses the boiling point curve and exacerbates the problem. Because it is difficult to completely vaporize the feedstream using only indirect heat exchange between the feedstream and the reactor effluent, a considerable amount of external heat provided by heating the feedstream with steam is required to insure that the feedstream is fully vaporized prior to introducing the feedstream to the reaction zone. The reaction zone can comprise either a fixed bed or a fluidized reaction zone, but a fluidized reaction zone is preferred.

Figure 2:
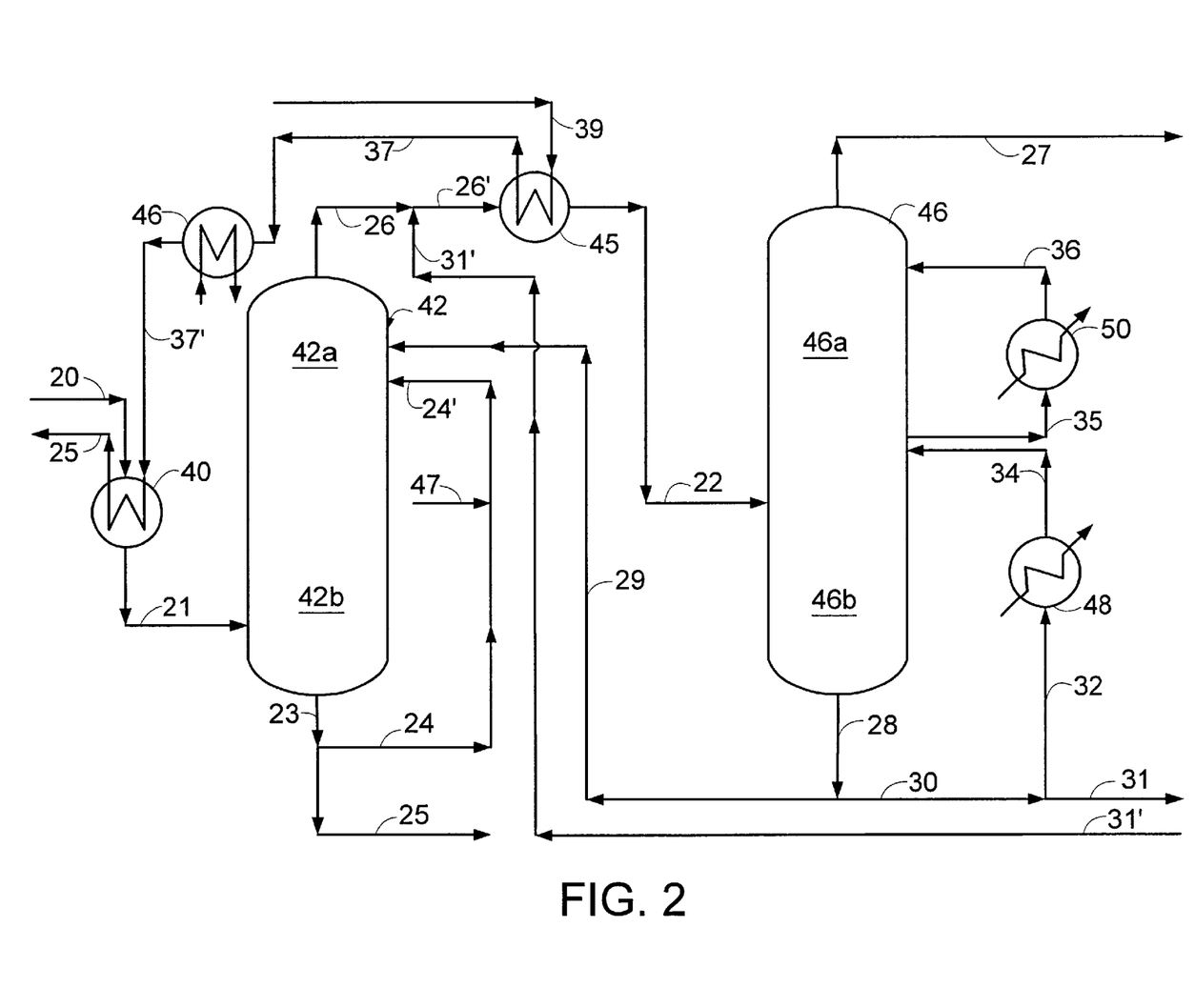
FIG. 2 is a schematic process flow diagram showing the present invention.
Figure 3:
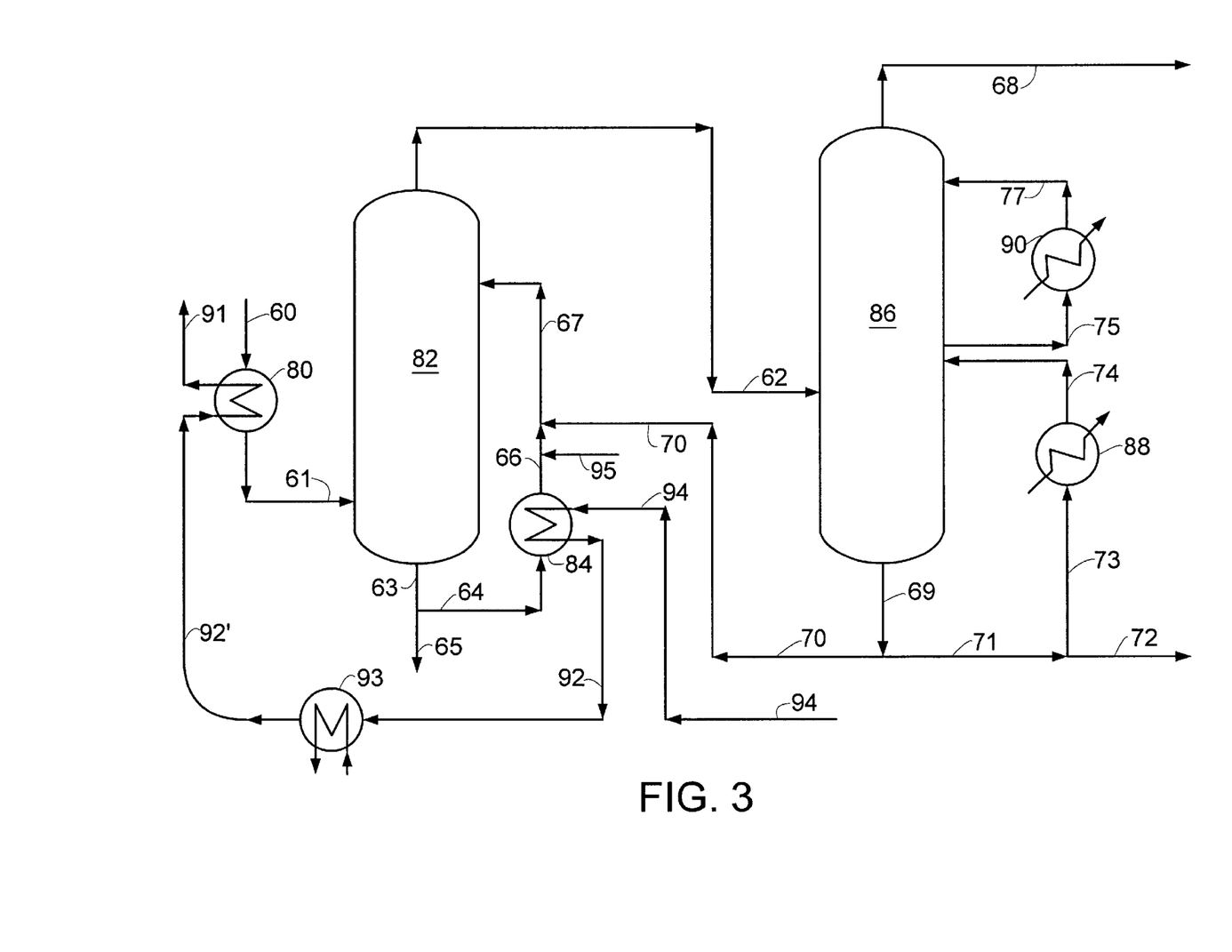
FIG. 3 is a schematic process flow diagram showing an alternate embodiment of the present invention.

In the operation of conventional quench systems, essentially all of the water withdrawn from the bottom of the quench tower is contaminated and must undergo further treatment before it can be returned to the process and the pumparound is cooled by indirect heat exchange with the feedstream. The present invention significantly reduces the treatment requirement for quench tower bottoms, provides purified water for immediate process to reduce the overall utility requirements of the process, and reduces the steam required to fully vaporize the feedstream. In the present invention, the reactor effluent is desuperheated and passed to a first stage quench tower. In one embodiment, a hydrocarbon vapor stream, comprising light olefins and water, is withdrawn from the top of the first stage quench tower and heat exchanged indirectly in an intercondenser with a portion of the feedstream to cool or at least partially condense the hydrocarbon vapor stream and provide a portion of the heat of the reaction to heat the feedstream. The subsequently cooled or at least partially condensed hydrocarbon vapors are passed to a second stage separation tower, or product separator, to further reduce the amount of water in the hydrocarbon vapor stream. A light olefin vapor stream is recovered from the top of the second stage separation tower, and a relatively pure aqueous stream, or purified water stream, is recovered from the bottom of the second stage separation tower. A portion of the purified water stream is returned to the first stage quench tower and the remaining portion is passed to a water stripper zone wherein any remaining oxygenates such as dimethyl ether and methanol and small amounts of light hydrocarbons such as propane are removed from the purified water stream as a stripper overhead stream, and a high purity product water stream is removed from the bottom of the water stripper zone. The stripper overhead stream is combined with the hydrocarbon vapors withdrawn from the top of the first stage quench tower prior to the exchange with the feedstream portion. The present invention may include either the intercondenser as described herein above to indirectly exchange heat between a preheated feedstream and an overhead stream withdrawn from the first stage quench tower of the two-stage quench system, or include an intercooler which indirectly exchanges heat between a preheated feedstream and that portion of the bottom of the first stage quench tower which is cooled and returned to the first stage quench tower as a first stage pumparound stream. These schemes are shown in FIG. 2 and FIG. 3, respectively. In both schemes, a portion of the water in the reactor effluent stream is condensed and removed from the process from the bottom of the first stage quench tower as a relatively small drag stream comprising impurities, catalyst fines, and neutralized organic acids. In both schemes, the drag stream withdrawn from the first stage tower is less than 20 weight percent of the total recovered water which is the combination of the drag stream and the net, or highly purified water removed from the water stripper column. Preferably, the drag stream withdrawn from the first stage tower bottoms stream comprises at least 5 weight percent and less than about 15 weight percent of the total recovered water; and more preferably, the drag stream withdrawn from the first stage tower bottoms stream comprises less than about 10 weight percent of the total recovered water. In both schemes it was discovered that organic acids such as acetic acid, formic acid, and propanoic acid were present in the reactor effluent stream and that these organic acids could be neutralized by the injection of a neutralization material into the first stage pumparound stream. In this matter, any organic acid is neutralized and removed in the drag stream as a dissolved salt. By removing the acid at this point in the process, corrosion and fouling problems throughout the remainder of the product recovery train are mitigated at an early point in the process scheme. It is preferable that the neutralization material comprises caustic, although ammonia or amines or mixtures thereof can be employed.

The scheme illustrated in FIG. 2 which includes an intercondenser offers the greatest energy savings. An unexpected advantage of the FIG. 2 scheme which employs the intercondenser is that the return of the purified water to the first stage quench tower and the drag stream are de-coupled. This de-coupling allows the drag stream flow in line 25 (FIG. 2) to be independently controlled to adjust of the quality of the purified water produced from the second stage tower or product separator 46 (FIG. 2). Thus, the scheme shown in FIG. 2 permits the greatest flexibility in process operation to control the removal of impurities and water from the hydrocarbon product. The present invention significantly reduces the amount of impurity containing water to be treated by concentrating essentially all of the impurities, catalyst fines, and neutralized organic acids into a very small drag stream. Furthermore, the present invention improves the energy-efficiency of the overall process by ensuring that the indirect heat exchange between the reactor effluent and the feedstream takes place in a condensing vapor/boiling liquid exchanger which provides the maximum overall transfer between these streams in the feed superheater, thereby reducing the considerable steam requirement and totally vaporizing the feedstream prior to entering the reactor. The term "superheat" as used herein refers to the thermodynamic condition of a stream which is heated to conditions above the point where the stream is essentially all vapor.

An alternative method of vaporizing a portion of the feedstream comprises passing a portion of the feedstream to the water stripping column and withdrawing a portion of the water stripper overhead stream comprising the vaporized oxygenate and passing a portion of the water stripper overhead stream to the exothermic reaction zone.

DETAILED DESCRIPTION OF THE DRAWINGS

The following description of the present process is made with reference to the drawings. In the interest of simplifying the description of the invention, the process system in the drawing does not contain the several conduits, valves, heat exchangers, and the like which—in actual practice—would be provided in accordance with routine skill in the art to enable the process to be carried out on a continuous basis.

Figure 1:
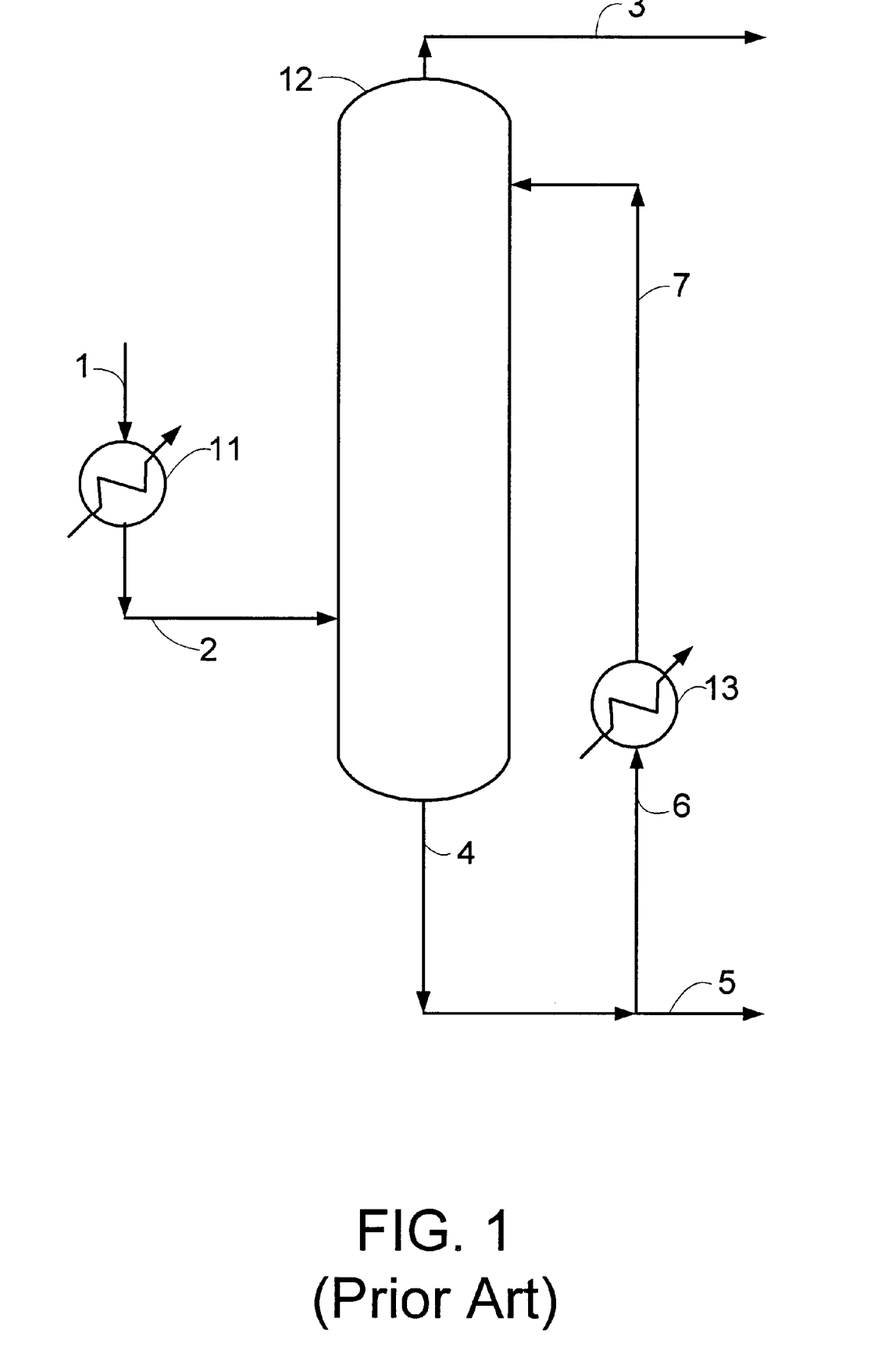
FIG. 1 is a schematic process flow diagram illustrating the prior art.

FIG. 1 illustrates the prior art approach to quenching the fluidized reactor effluent from the oxygenate conversion process. An example of such an approach is disclosed in publication WO 99/55650. With reference to FIG. 1, the reactor effluent in line 1 is passed to a feed/effluent exchanger 11 to indirectly transfer a portion of the heat of reaction from the reactor effluent to the feedstock charged to the reactor to provide a cooled reactor effluent stream in line 2. The cooled reactor effluent stream in line 2 is passed to the water quench tower 12 to provide an olefinic overhead stream in line 3 and an aqueous stream in line 4. A portion of the aqueous stream in line 5 is withdrawn via lines 4 and 5 as an aqueous waste stream, and a portion of the aqueous stream in line 4 is passed via line 6 to a cooler 13 to provide a cooled pumparound stream in line 7 which is returned to the water quench tower 12 at a point above the point where the reactor effluent stream in line 2 was introduced.

The two-stage quench process of the present invention is illustrated in FIG. 2 wherein a reactor effluent stream in line 20 at reactor effluent conditions including a temperature ranging from 250° to 550° C. is passed to a feed superheater, or feed/effluent exchanger 40 to cool the reactor effluent stream to provide a cooled reactor effluent stream in line 21. The cooled reactor effluent stream in line 21 is introduced to a first stage quench tower 42 having an upper portion 42a and a lower portion 42b. In the first stage quench tower 42, the cooled reactor effluent stream in line 21 which is introduced in the lower portion 42b of the first stage quench tower is contacted with a pumparound stream introduced in line 24' to produce a first stage overhead stream in line 26 withdrawn from the upper portion 42a of the first stage quench tower and comprising a reduced amount of water relative to the cooled reactor effluent stream. An aqueous stream, or first stage quench tower bottoms stream, (comprising water, impurities, oxygenates, and catalyst fines) in line 23 is withdrawn from the lower portion 42b of the first stage quench tower 42. At least a portion of the aqueous stream is withdrawn from the process via line 23 and line 25 as an aqueous waste stream, or a drag stream, and passed for further treatment to a water treatment zone (not shown). The impurities in the drag stream include neutralized acids (organic salts). The neutralized acids result from the injection of an effective amount of a neutralizing stream in line 47 into the pumparound stream in line 24 to neutralize organic acids to prevent corrosion and fouling in the first and second stage quench towers. The drag stream, or the aqueous waste stream, comprises the majority of the impurities and catalyst fines, now concentrated into a small drag stream which comprises between about 5 and about 10 weight percent of the total recovered water. The remaining portion of the aqueous stream in line 23 returned to the first stage quench tower 42 via lines 24 and 24' as the pumparound stream. The first stage overhead stream in line 26 is passed via lines 26 and 26' to an intercondenser 45 wherein the first stage overhead stream is cooled by indirect heat exchange to provide a cooled first stage overhead stream in line 22. A water stripper overhead stream in line 31' which is essentially all vapor is withdrawn from a water stripper column (not shown) and admixed with the first stage overhead stream in line 26 prior to passing the first stage overhead stream to the intercondenser 45 via lines 26 and 26'.

The cooling of the first stage overhead stream in line 26' and the reactor effluent stream in line 20 is provided by a novel heat exchange sequence which is only made possible by the present invention. Accordingly, a preheated feedstream in line 39 comprising an oxygenate and up to about 30 weight percent water is passed to a feed side of the intercondenser 45 to cool the first stage overhead stream in line 26' by indirect heat exchange with the preheated feedstream in line 39 to provide a partially vaporized feedstream in line 37 and the cooled first stage overhead stream in line 22. The partially vaporized feedstream in line 37 is passed to a feed vaporizer 46 to essentially fully vaporize the feedstream and produce a vaporized feedstream in line 37'. The vaporized feedstream in line 37' is passed to the feed superheater 40. The feed superheater 40 is a preferably a vertical exchanger having a feed side and an effluent side. In the feed superheater 40, the reactor effluent stream in line 20, a superheated vapor stream, is indirectly heat exchanged with a fully vaporized feedstream in line 37' to desuperheat the reactor effluent stream and to superheat the feedstream prior to passing the superheated feedstream in line 25 to the oxygenate conversion zone (not shown in FIG. 2).

The cooled first stage overhead stream in line 22 is passed to a second stage tower, or product separator 46, having an upper separation zone 46a and a lower separation zone 46b, the product separator providing a second-stage overhead stream comprising light olefins in line 27 and a purified water stream comprising less than 10 about 10,000 ppm-wt oxygenates in line 28. Following conventional water stripping in a water stripper column to strip oxygenates from the purified water stream to provide a highly purified water stream, the highly purified water stream comprises less than about 500 ppm-wt oxygenates, and more preferably, after conventional water stripping, the highly purified water stream comprises between about 10 and about 100 ppm-wt oxygenates. At least a portion of the purified water stream is returned to the first stage tower via lines 28 and 29 as a quench tower make up stream, and a portion of the purified water stream is withdrawn from the lower separation zone 46b via lines 30 and 31 as a net purified water stream. The net purified water stream in line 31 is passed to the water stripper column (not shown) and a water stripper overhead stream is returned in line 31' as described hereinabove. A second portion of the purified water stream is conducted via lines 30 and 32 as a first separator pumparound stream to a secondary heat exchanger 48 to produce a first cooled purified water stream in line 34. The first cooled purified water stream is returned to the second-stage tower 46 at a point above the point where the first stage overhead stream in line 22 was introduced at the upper portion of the lower separation zone 46b. A side draw stream in line 35 is withdrawn from a lower portion of the upper separation zone 46a and passed to a tertiary heat exchanger 50 to provide a second cooled water stream, or second separator pumparound stream in line 36 which is returned to second-stage tower 46 in the upper separation zone 46a. The secondary heat exchanger 48 can be a product heat exchanger in an olefin separation zone (not shown) wherein the purified water stream in line 32 is cooled by indirect heat exchange to provide the first cooled purified water stream in line 34.

Referring now to FIG. 3 which is an alternate embodiment of the present invention, the partial vaporization of the preheated feedstream is performed in an intercooler 84 which cools a portion of the first stage quench tower bottoms stream in line 64 by indirect heat exchange with the preheated feedstream in line 94. According to FIG. 3, a reactor effluent stream in line 60 is passed to a feed superheater 80 wherein the reactor effluent stream is desuperheated and passed in line 61 to a first stage quench tower 82. The first stage quench tower 82 is part of a two-stage quench zone comprising the first stage quench tower 82 and a second stage tower 86, or product separator. A purified water stream in line 67 is passed to an upper portion of the first stage quench tower 82 and an overhead stream in line 62 is recovered. The overhead stream in line 62 comprises light olefins and water. A first stage bottoms stream in line 63 is removed from the bottom of the first stage quench tower 82. The first stage bottoms stream comprises impurities, catalyst particles, and water. A first portion of the first stage bottoms stream is withdrawn from the process as a drag stream in line 65. A second portion of the first stage bottoms stream is passed via lines 63 and 64 to an intercooler 84 which cools the second portion of the first stage bottoms stream by indirect heat exchange as described hereinabove to provide a cooled first stage bottoms stream in line 66. A neutralizing stream in line 95 is injected into line 66 to neutralize organic acid impurities such as acetic, formic, and propanoic acids which were surprisingly discovered in the reactor effluent and converts the organic acids to organic salts. The neutralizing stream is selected from the group consisting of caustic, ammonia, and amines. The cooled first stage bottoms stream in line 66 and when required a second stage purified water stream in line 70 are admixed to provide the purified water stream in line 67 which is returned to an upper portion of the first stage quench tower 82. The flow of the second stage purified water stream in line 70 is not a normal flow; it is only required when an insufficient amount of heat is removed by the intercooler 84. The overhead stream in line 62 is passed to the second stage tower 86, or product separator, and therein contacted with a cooled purified water stream in line to further separate water from the first stage overhead stream to produce a light olefin product stream in line 68 and a purified water stream in line 69. A first portion of the purified water stream in line 69 is returned to the first stage quench tower as described hereinabove via line 70. A second portion of the purified water stream is passed via lines 69, 71, and 73 to a primary second stage exchanger 88 to provide the cooled purified water stream in line 74. The cooled purified water stream in line 74 is returned to a lower portion of the second stage tower at a point above a point where the first stage overhead stream was introduced to the second stage tower 86. A side draw stream in line 75 is withdrawn from the second stage tower 86 at a point above the return of line 74 and passed to a secondary exchanger 90 to cool the side draw stream and provide a second cooled water stream in line 77. The second cooled water stream in line 77 is returned to the top of the second stage tower. A third portion of the purified water stream in line 69 is withdrawn via lines 69, 71, and 72 to a water stripping zone (not shown) wherein the purified water stream is stripped to produce a high purity water stream comprising less than about 500 ppm-wt oxygenates. Preferably, the high purity water stream comprises between about 10 and about 100 ppm-wt oxygenates. According to FIG. 3, the preheated feedstream in line 94 is passed to the intercooler 84 to cool the first stage bottoms stream and at least partially vaporize the feedstream to provide a partially vaporized feedstream in line 92. The partially vaporized feedstream in line 92 is passed to a feed vaporizer 93 which substantially vaporizes the feedstream to provide a vaporized feedstream in line 92'. The vaporized feedstream in line 92' is passed to the feed side of the feed superheater 80 to superheat the feedstream to produce a superheated feedstream in line 91, which can now be passed to the MTO reactor (not shown), and to desuperheat the reactor effluent stream in line 60. The light olefin product stream in line 68 is passed to a product separation zone (not shown) for the separation of individual olefin products. The olefin products include ethylene, propylene, and butylenes.

Figure 4:
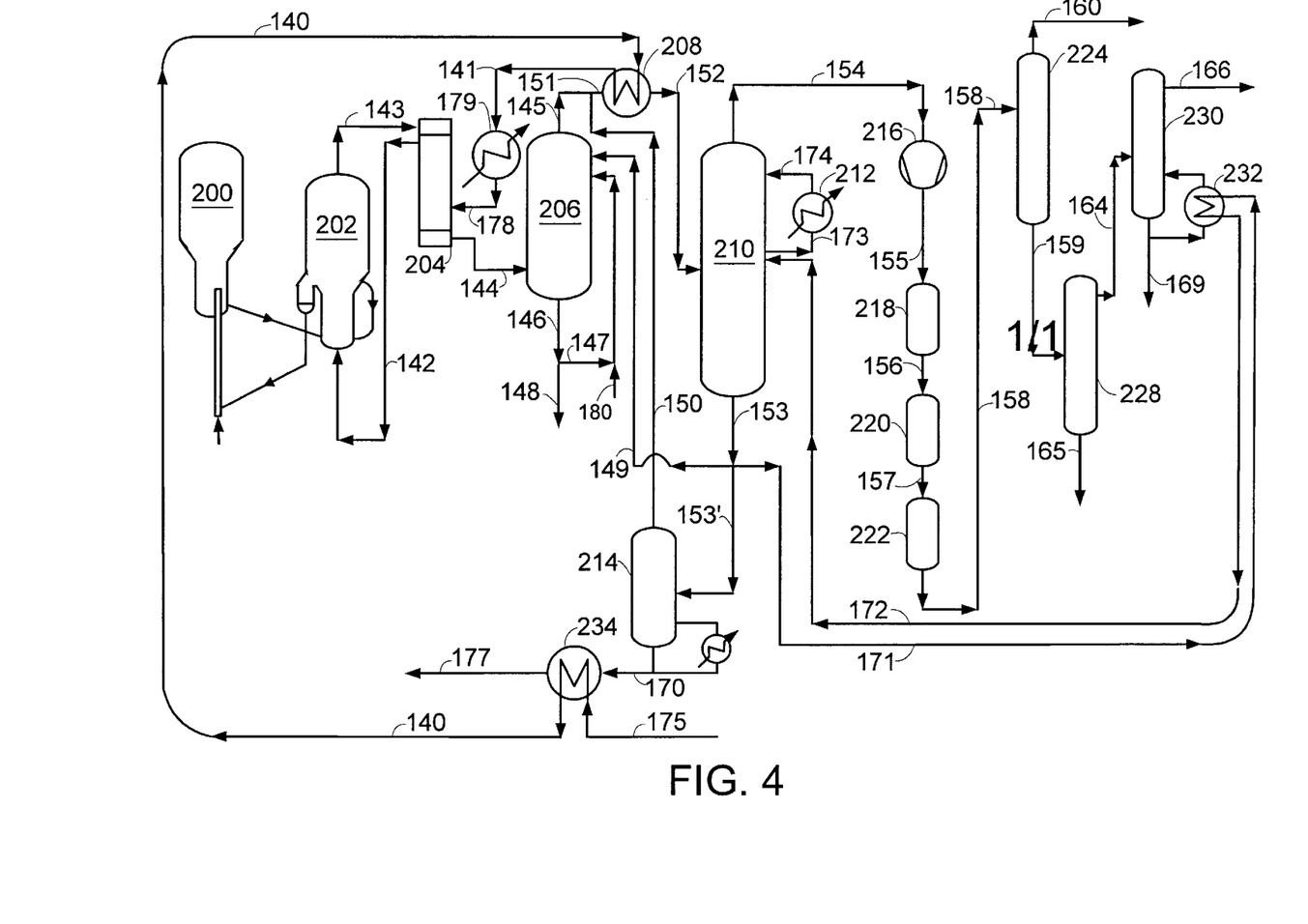
FIG. 4 is a schematic process flow diagram showing the preferred embodiment and the integrated oxygenate conversion process.

FIG. 4 represents and integration of the present invention as depicted in FIG. 2 with a complex for the production of propylene from a system to the conversion of oxygenates into light olefin products. Referring to FIG. 4, a feedstream in line 175 is passed to a feed preheater 234 to provide a preheated feedstream in line 140. The preheated feedstream in line 140 is passed to an intercondenser 208 to partially vaporize the preheated feedstream to provide a partially vaporized feedstream in line 141. The partially vaporized feedstream in line 141 is passed to a feed vaporizer 179 which substantially vaporizes the feedstream to provide a vaporized feedstream in line 178. The vaporized feedstream in line 178 is passed to a feed side of a feed superheater 204 to superheat the feedstream to provide a superheated feedstream in line 142 by indirect exchange with the reactor effluent stream in line 143. The reactor effluent stream in line 143 is withdrawn from an oxygenate conversion reaction zone 202 which contains a fluidized catalyst which is periodically or continuously circulated in a conventional manner to the regeneration zone 200 to maintain the selectivity and the conversion desired. Reaction zone 202 is maintained at effective conditions for the conversion of the oxygenate to produce light olefin products. The reactor effluent stream comprises light olefins, water, impurities, unreacted oxygenates, and catalyst fines. In the feed superheater 204, the reactor effluent stream is desuperheated to produce a desuperheated vapor effluent stream in line 144. The desuperheated vapor effluent stream in line 144 is passed to a first stage quench tower 206 of a two-stage quench zone containing the first stage quench tower 206 and a second stage tower or product separator 210. In the first stage quench tower 206, the desuperheated vapor effluent stream is contacted with a purified water stream in line 149 which is introduced at the top, or upper portion of the first stage quench tower 206. A first stage overhead stream in line 145 is withdrawn from the first stage quench tower 206 and passed via lines 145 and 151 to an intercondenser 208 to provide a cooled first stage overhead stream in line 152. The intercondenser 208 provides indirect heat transfer between the preheated feedstream in line 140 and the first stage quench tower overhead stream in line 151 to partially vaporize the preheated feedstream and cool the first stage overhead stream. A first stage bottoms stream comprising catalyst fines, impurities, and water is withdrawn from the first stage quench tower 206 via line 146 and a portion of which is withdrawn as a drag stream in line 148. The drag stream in line comprises from about 5 to about 15 weight percent of the total recovered water which is the sum of the drag stream and the highly purified water stream in line 177 which is withdrawn from the water stripper column 214. The remaining portion of the first stage bottoms stream is injected with a neutralizing stream in line 180 and returned to an upper portion of the first stage quench tower in line 147 as a quench pumparound stream. The cooled first stage overhead stream in line 152 is passed to the second stage tower 210, or product separator, to separate the light olefins from water to provide a vapor product stream in line 154 comprising light olefins, and a purified water stream in line 153. A first portion of the purified water stream is returned to the upper portion of the first stage quench tower via lines 153 and 149. A second portion of the purified water stream in line 153 is passed via line 171 to a product heat exchanger 232 to provide a cooled purified water stream in line 172. The cooled purified water stream in line 172 is returned to an upper portion of the second stage tower 210. A third portion of the purified water stream is passed via lines 153 and 153' to a water stripper column 214 to provide a water stripper overhead stream in line 150 and a highly purified water stream in line 170. The highly purified water stream in line 170 is passed to feed preheater 234 to further cool the highly purified water stream to provide a cooled highly purified water stream in line 177 while simultaneously preheating the feedstream in line 175 by indirect exchange. The water stripper overhead stream in line 150 is admixed with the first stage overhead stream in line 145 prior to introducing the first stage overhead stream to the intercondenser 208 via line 151. The highly purified water stream in line 177 will have an oxygenate content less than 500 ppm-wt. The highly purified water stream can be withdrawn for reuse anywhere in the process as pure water or treated further in a conventional molecular sieve adsorption process to further reduce the oxygenate content in a manner well known to those skilled in the art.

The vapor product stream in line 154 is passed to a series of steps to produce the individual light olefin products. Initially, the vapor product stream is passed to a compression zone 216 to provide a compressed olefin stream in line 155. The compressed olefin stream in line 155 is passed to an oxygenate removal zone 218 for the removal of any unreacted oxygenates. The oxygenate removal zone 218 can comprise either a conventional absorption based process or a conventional adsorption process using a molecular sieve to selectively remove oxygenates. An essentially oxygenate-free stream is withdrawn from the oxygenate removal zone in line 156 and passed to a caustic wash zone 220 wherein the essentially oxygenate-free stream is contacted with an aqueous caustic solution to remove carbon dioxide. An essentially carbon dioxide free light olefin stream is withdrawn in line 157 and passed to a dryer zone 222 for the removal of water. The dryer zone 222 comprises a conventional desiccant dryer system employing a molecular sieve. A dry olefinic product stream is withdrawn from the dryer zone in line 158 and passed to a conventional light olefin recovery zone which is illustrated by a deethanizer zone 224 wherein a stream comprising components with boiling points lower than propylene, or a propylene and heavier stream, is withdrawn from the deethanizer zone 224 in line 160 and passed to further ethylene recovery (not shown). A propylene and heavier stream is withdrawn from the deethanizer zone and passed via line 164 to a depropanizer zone 228. In the depropanizer zone 228, a $C_3$ hydrocarbon stream comprising propane and propylene is separated from a $C_4^+$ stream in line 165 having boiling points heavier than propane. The $C_4^+$ stream in line 165 is withdrawn for further recovery of butylenes. The $C_3$ hydrocarbon stream is passed to a propane/propylene splitter reboiler 230 to separate a high purity propylene product (greater than 95 mole percent propylene) in line 166 from a propane stream in line 169. According to the present invention, the second portion of the purified water stream in line 171 is employed to heat the propane/propylene splitter reboiler 230, or product heat exchanger, thereby cooling the third portion of the purified water stream to provide the cooled purified water stream in line 172.

The following examples are only intended to illustrate the present invention and are not meant to be limiting. The examples are based on an engineering simulation of the oxygenate conversion complex.

EXAMPLES

Example I

Column A of Table 1 shows the key process heat exchangers and specific energy inputs to a prior art complex which uses a single stage quench tower in the production of about 1.2 metric tonnes per annum of light olefins by the conversion of a methanol feedstream. The key process heat exchangers include a feed preheater which heats the feed by indirect exchange with stripped waste water streams; an intercooler which exchanges heat between the preheated feedstream and the recirculated quench tower bottoms stream; and a feed superheater which exchanges heat with the reactor effluent. The heat input to the process includes a feed vaporizer to vaporize the feed prior to indirect heat exchange with the reactor effluent; a feed stripper reboiler which supplies heat for the separation of oxygenates from the quench tower bottoms stream; and, heat recovered from the use of a catalyst cooler in the reaction zone. The methanol feedstream comprises crude methanol having about 82 weight percent methanol and about 18 weight percent water. In the prior art scheme, the methanol feedstream is converted in a fluidized reaction zone over a SAPO-34 non-zeolitic catalyst at an operating pressure of about 200 to about 350 kPa (30 to 50 psia) and a temperature of about 450° to about 480° C. to produce a reactor effluent stream comprising about an equal amount of ethylene and propylene. The prior art scheme requires an overall energy input of about 150 gJoules (giga-Joules) per hour and for comparison purposes is shown as with relative energy requirement for the conventionally operated single column quench scheme as a value of 1.0.

TABLE 1

Relative Heat Exchanger Capacity and Energy Input Comparison

| Heat Exchanger | A<br>Prior Art | B<br>Two-Stage<br>Quench | C<br>2-Stage Quench<br>& Intercondenser |
|---|---|---|---|
| Process Heat Exchanger Rating | | | |
| Feed Pre-heater | 1 | 0.91 | 0.96 |
| Intercooler (Quench Tower Bottoms) | 1 | 1.0 | none |
| Intercondenser | none | none | yes |
| Feed Superheater | 1 | 1.0 | 0.99 |
| Energy Input to Process | | | |
| Feed Vaporizer | 1 | 1.02 | 0.67 |
| Feed Stripper | 1 | 1.0 | 1.03 |
| Total Energy Input, gJoule/hr | 149 | 155 | 125 |
| Total Relative Energy Input | 1 | 1.04 | 0.83 |

Example II

The prior art scheme described with respect to column A of Table 1 was modified to include the two-stage quench scheme described with reference to FIG. 3. Column B of Table 1 shows the impact of the two-stage quench scheme with an intercooler (as described in reference to FIG. 3.) on the individual process exchangers and the overall energy requirements of the oxygenate conversion complex relative to the prior art scheme of Example I. Although the two-stage quench scheme with the intercooler significantly reduces the amount of waste water to be treated, it requires about a 4 percent increase in the total energy input to the process. Thus, a 90 percent reduction in the production of waste water is achieved, but there is no energy advantage for the change from a single column to a two-stage quench zone.

Example III

The prior art scheme of column A was again modified to correspond to the two-stage quench scheme of the present invention as disclosed in FIG. 2. Column C of Table illustrates the impact of the addition of the intercondenser to the two-stage quench scheme. The addition of the intercondenser to the two-stage quench scheme achieves the 90 percent decrease in the waste water production, and in addition results in a more overall energy efficient process. As shown by a comparison of the prior art scheme in column A and that of the present invention according to FIG. 2 as shown in column C, the total relative energy input shows about an unexpected 17 percent advantage over the prior art for the scheme using the two-stage quench scheme with the intercondenser. It is believed that a portion of this advantage is achieved by using heat recovered from the first stage quench tower overhead stream to partially vaporize the preheated feedstream which reduced the need for external heat to fully vaporize the feedstream prior to the indirect heat exchange and improves the efficiency of the indirect heat exchange between the fully vaporized feedstream and the reactor effluent.

Example IV

The presence of water in the feedstream during the preheating, vaporizing, and superheating steps can have a profound influence on the total energy input to the process. Removal of the associated water will result in a significant improvement in the energy efficiency of the overall complex. Table 2 shows about a 50 percent energy advantage in the relative energy input between the process of the present invention for an essentially pure methanol feed (99.85 percent methanol) in column D over the prior art single quench column scheme as shown in column A. In order to achieve this advantage, the size of the intercondenser increases to more than twice the capacity of the intercondenser in column C of Table 1. Thus, there is an advantage to limit the amount of water in the crude methanol in the feedstream to a value between about 0.001 and about 30 weight percent to achieve the benefit of the present invention over the prior art.

TABLE 2

Pure Methanol Feed Comparison with Prior Art

| Heat Exchanger | A<br>Prior Art | D<br>2-Stage Quench<br>& Intercondenser |
|---|---|---|
| Process Heat Exchanger Rating | | |
| Feed Pre-heater | 1 | 0.83 |
| Intercooler (Quench Tower Bottoms) | 1 | none |
| Intercondenser | none | yes |
| Feed Superheater | 1 | 0.07 |
| Energy Input to Process | | |
| Feed Vaporizer | 1 | 0.19 |
| Feed Stripper | 1 | 0.96 |
| Total Energy Input, gJoule/hr | 149 | 73.2 |
| Total Relative Energy Input | 1 | 0.49 |

Example V

The present invention's use of the intercondenser decouples the drag stream and purified water recycle to the first stage quench tower. A comparison of the schemes of the present invention (B–D corresponding to the columns B–D in Tables 1 and 2) with the single stage quench tower (A) of the prior art is shown in Table 3 to illustrate the drag stream.

In Table 3, the relative flow rates are expressed in weight fractions of the reactor effluent flow. The pumparound in the single stage quench tower and in the first stage quench tower ranged from about 4:1 to about 6:1. The drag stream withdrawal from the two-stage quench zone ranged from about 0.04 to 0.05. In Cases B, C, and D, the stripped water now can be upgraded to boiler feed water quality because the higher boiling contaminants have been removed in the drag stream.

TABLE 3

Comparison of Capacity/Flow Rates
(Shown as Weight Fraction of Reactor Effluent)

|  | A | B | C | D |
|---|---|---|---|---|
| Reactor Effluent | 1 | 1 | 1 | 0.84 |
| Purified Water to First Stage | — | — | 0.06 | 0.34 |
| Quench Tower Pumparound | 6 | 6 | 6 | 5 |
| Drag Stream | — | 0.05 | 0.05 | 0.04 |
| Overhead to Prod Separator | — | 0.95 | 1.01 | 1.15 |
| Vapor From Water Stripper | 0.09 | 0.10 | 0.10 | 0.08 |
| Stripped Water | 0.60 | 0.54 | 0.54 | 0.47 |
| Separator Overhead Product | 0.39 | 0.39 | 0.39 | 0.40 |

What is claimed is:

1. A two-stage quench tower process for removing impurities from a superheated reactor effluent stream withdrawn from an oxygenate conversion complex, said process comprising:

a) passing the superheated reactor effluent stream comprising light olefin, water, and organic acids to a feed/effluent exchanger to desuperheat said reactor effluent stream by indirect exchange with a vaporized feedstream to provide a desuperheated stream;

b) passing the desuperheated stream to a first tower of a two-stage quench zone containing a first tower and a second tower, and contacting therein the desuperheated stream in an upper portion of the first tower with a neutralized water stream to condense at least a portion of the water to provide a first stage bottoms stream comprising water and neutralized organic acids and a first stage overhead stream comprising light olefins and water;

c) passing the first stage overhead stream to the second tower and therein contacting the first stage overhead stream with a cooled purified water stream to provide a light olefin product stream and a purified water stream;

d) cooling a first portion of the purified water stream to provide the cooled purified water stream;

e) passing a second portion of the purified water stream to a water stripper column to provide a high purity water stream and a stripper overhead stream, admixing the stripper overhead stream with the first stage overhead stream, and cooling the first stage overhead stream prior to step (c), or passing a second portion of the purified water stream to a water stripper to provide a high purity water stream and a stripper overhead stream, cooling a portion of the first stage bottoms stream and admixing a neutralization stream and a third portion of the purified water stream therewith to provide the neutralized water stream, and admixing the stripper overhead stream with the first stage overhead stream; and f) returning a fourth portion of the purified water stream to the first tower.

2. A process for removing a contaminated water stream from a reactor effluent stream from an oxygenate conversion reactor comprising light olefins, water and impurities withdrawn from a fluidized exothermic reaction zone, said process comprising:

a) contacting the reactor effluent stream with an aqueous recycle stream in a fast stage tower of a two-stage quench zone having the first stage tower and a second stage tower to provide the contaminated water stream comprising the impurities and a first stage overhead stream comprising light olefins and water;

b) passing the light olefin stream to the second stage tower to provide a light olefin stream and a purified water stream; and c) returning at least a portion of the purified water stream to the first stage tower to provide the aqueous recycle stream; and d) passing the purified water stream to a water stripper zone to provide a stripper overhead stream and a high purity water stream and admixing at least a portion of the stripper overhead stream with the first stage overhead stream prior to passing the first stage overhead stream to the second stage tower.

3. The process of claim 2 wherein the reactor effluent stream is contacted with the aqueous recycle stream in an upper portion of the first stage tower.

4. The process of claim 2 further comprising passing a neutralization stream to the first stage tower to neutralize at least a portion of the impurities.

5. A process for removing a contaminated water stream from a reactor effluent stream from an oxygenate conversion reactor comprising light olefins, water and impurities withdrawn from a fluidized exothermic reaction zone, said process comprising:

a) contacting the reactor effluent stream with an aqueous recycle stream in a first stage tower of a two-stage quench zone having the first stage tower and a second stage tower to provide the contaminated water stream comprising the impurities and a first stage overhead stream comprising light olefins and water;

b) passing the light olefin stream to the second stage tower to provide a light olefin stream and a purified water stream; and c) returning at least a portion of the purified water stream to the first stage tower to provide the aqueous recycle stream; and d) passing the light olefin stream to a fractionation zone comprising a propane/propylene splitter having a reboiler and heating the reboiler by indirect heat exchange with at least a portion of the purified water stream.

6. The process of claim 5 further comprising returning at least a portion of the cooled purified water stream to the second stage tower.

7. The process of claim 2 wherein the impurities are selected from the group consisting of ethers, alcohols, aldehydes, organic acids and mixtures thereof.

8. The process of claim 2 wherein the contaminated water stream comprises less than about 15 weight percent of a total recovered water stream comprising the highly purified water stream and the contaminated water stream.

* * * * *